US012778570B2

(12) United States Patent
Riemhofer et al.

(10) Patent No.: US 12,778,570 B2
(45) Date of Patent: Nov. 3, 2026

(54) TRANSMISSION ASSEMBLY

(71) Applicant: NuVasive, INC., San Diego, CA (US)

(72) Inventors: Byron Riemhofer, San Diego, CA (US); Andrew Morris, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 12 days.

(21) Appl. No.: 19/170,156

(22) Filed: Apr. 4, 2025

(65) Prior Publication Data

US 2025/0228543 A1 Jul. 17, 2025

Related U.S. Application Data

(63) Continuation of application No. 18/168,371, filed on Feb. 13, 2023, now Pat. No. 12,274,429, which is a continuation of application No. 16/854,782, filed on Apr. 21, 2020, now Pat. No. 11,602,337.

(60) Provisional application No. 62/838,284, filed on Apr. 24, 2019.

(51) Int. Cl.

| | |
|---|---|
| ***A61B 17/02*** | (2006.01) |
| ***A61B 17/00*** | (2006.01) |
| ***A61B 17/70*** | (2006.01) |
| ***F16D 21/02*** | (2006.01) |

(52) U.S. Cl.

CPC .......... *A61B 17/0218* (2013.01); *A61B 17/02* (2013.01); *A61B 17/0206* (2013.01); *A61B 17/7082* (2013.01); *F16D 21/02* (2013.01); *A61B 2017/00393* (2013.01)

(58) Field of Classification Search

CPC ............... F16D 21/02; F16D 2023/123; F16D 2125/28; F16H 37/065; F16H 37/124; F16H 37/12; F16H 57/023

See application file for complete search history.

(56) References Cited

U.S. PATENT DOCUMENTS

| | | | | |
|---|---|---|---|---|
| 5,730,757 A * | 3/1998 | Benetti | A61B 90/50 | 606/198 |
| 6,074,343 A * | 6/2000 | Nathanson | A61B 17/0206 | 600/224 |
| 2005/0021040 A1* | 1/2005 | Bertagnoli | A61B 17/708 | 606/90 |
| 2012/0144943 A1* | 6/2012 | Shigematsu | F16H 37/065 | 74/335 |
| 2014/0114138 A1* | 4/2014 | Fedorov | A61B 17/0206 | 600/233 |

(Continued)

*Primary Examiner* — Eduardo C Robert
*Assistant Examiner* — Anna V. Little

(57) ABSTRACT

An assembly comprising a drive gear coupled to a shaft and a dial. The drive gear is configured to rotate along a first axis based on movement of the dial. The assembly includes a first linking member located along a second axis and configured to rotate about the second axis based on contact with the drive gear as the drive gear is rotated. The assembly includes a second linking member located along the second axis and configured to rotate about the second axis based on rotation of the drive gear and a coupling between the first linking member and the second linking member. The assembly includes a linking member selector configured to rotate about the first axis and for selecting at least a position corresponding to the first linking member that causes the coupling between the first linking member and the second linking member.

15 Claims, 11 Drawing Sheets

(56) References Cited

U.S. PATENT DOCUMENTS

| | | | | |
|---|---|---|---|---|
| 2014/0309500 | A1* | 10/2014 | Thompson ......... | A61B 17/0206 600/219 |
| 2015/0216517 | A1* | 8/2015 | Bjork ..................... | A61B 17/86 600/215 |
| 2018/0177499 | A1* | 6/2018 | Sauer ................. | A61B 17/0206 |

* cited by examiner

TRANSMISSION ASSEMBLY

CROSS-REFERENCE TO RELATED APPLICATION

This application is a continuation of U.S. patent application Ser. No. 18/168,371, filed on Feb. 13, 2023 and published as U.S. 2023-00200793, which is a continuation of U.S. patent application Ser. No. 16/854,782, filed Apr. 21, 2020 and now U.S. Ser. No. 11/602,337, which is a non-provisional patent application claiming the benefit of priority under 35 U.S.C. 119(c) from U.S. Provisional Patent Application Ser. No. 62/838,284, filed on Apr. 24, 2019, the entire contents of which are each hereby expressly incorporated by reference into this disclosure as if set forth fully herein.

FIELD

This disclosure describes an assembly for actuating components of a surgical instrument.

BACKGROUND

A noteworthy trend in the medical community is the move away from performing surgery via traditional "open" techniques in favor of minimally invasive or minimal access techniques. Open surgical techniques are less desirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements.

Currently available access systems require multiple inputs to actuate components in multiple directions or shifting the anchor point of the retractor from one position to another to create a customized exposure to the target surgical site. There exists a need for an access system that enables a surgeon to create a reproducible, customized exposure to the target surgical site in a faster and less complicated manner.

SUMMARY

In one embodiment, an assembly includes a dial and a shaft coupled to the dial. The assembly also includes a drive gear coupled to the shaft. The drive gear is configured to rotate along a first axis based on movement of the dial. The assembly also includes a first linking member located along a second axis and configured to rotate about the second axis based on contact with the drive gear as the drive gear is rotated. The second axis is perpendicular to the first axis. The assembly also includes a second linking member located about the second axis and configured to rotate about the second axis based on rotation of the drive gear and a coupling between the first linking member and the second linking member. The assembly also includes a linking member selector configured to rotate about the first axis. The linking member selector includes a handle for rotating the linking member selector and selecting at least a position corresponding to the first linking member. The linking member also includes a cylindrical body integrally formed with the handle. The cylindrical body includes an aperture along a longitudinal axis of the cylindrical body. The cylindrical body also includes at least one protrusion configured to exert a force on the first linking member based on selection, via the handle, of the position corresponding to the first linking member. The force exerted on the first linking member causes the coupling between the first linking member and the second linking member. The aperture is configured to receive the shaft.

In another embodiment, an assembly includes a dial and a shaft coupled to the dial. The assembly also includes a drive gear coupled to the shaft. The drive gear is configured to rotate along a first axis based on movement of the dial. The assembly also includes a plurality of linking members. The plurality of linking members includes a first linking member located along a second axis and configured to rotate about the second axis based on contact with the drive gear as the drive gear is rotated. The second axis is perpendicular to the first axis. The plurality of linking members also includes a second linking member located about the second axis and configured to rotate about the second axis based on rotation of the drive gear and a coupling between the first linking member and the second linking member. The plurality of linking members also includes a third linking member located along a third axis and configured to rotate about the third axis based on contact with the drive gear as the drive gear is rotated.

The third axis is perpendicular to the first axis and the second axis. The plurality of linking members also includes a fourth linking member located about the third axis and configured to rotate about the third axis based on rotation of the drive gear and a coupling between the third linking member and the fourth linking member. The assembly also includes a linking member selector configured to rotate about the first axis. The linking member selector includes a handle for rotating the linking member selector and selecting a position of a plurality of positions corresponding to the plurality of the linking members. The linking member selector also includes a cylindrical body integrally formed with the handle. The cylindrical body includes an aperture along a longitudinal axis of the cylindrical body. The cylindrical body also includes at least one protrusion configured to exert a force on at least one of the plurality of linking members based on selection, via the handle, of the position of the plurality of positions corresponding to the first linking member and the third linking member. The aperture is configured to receive the shaft.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Figure 1:
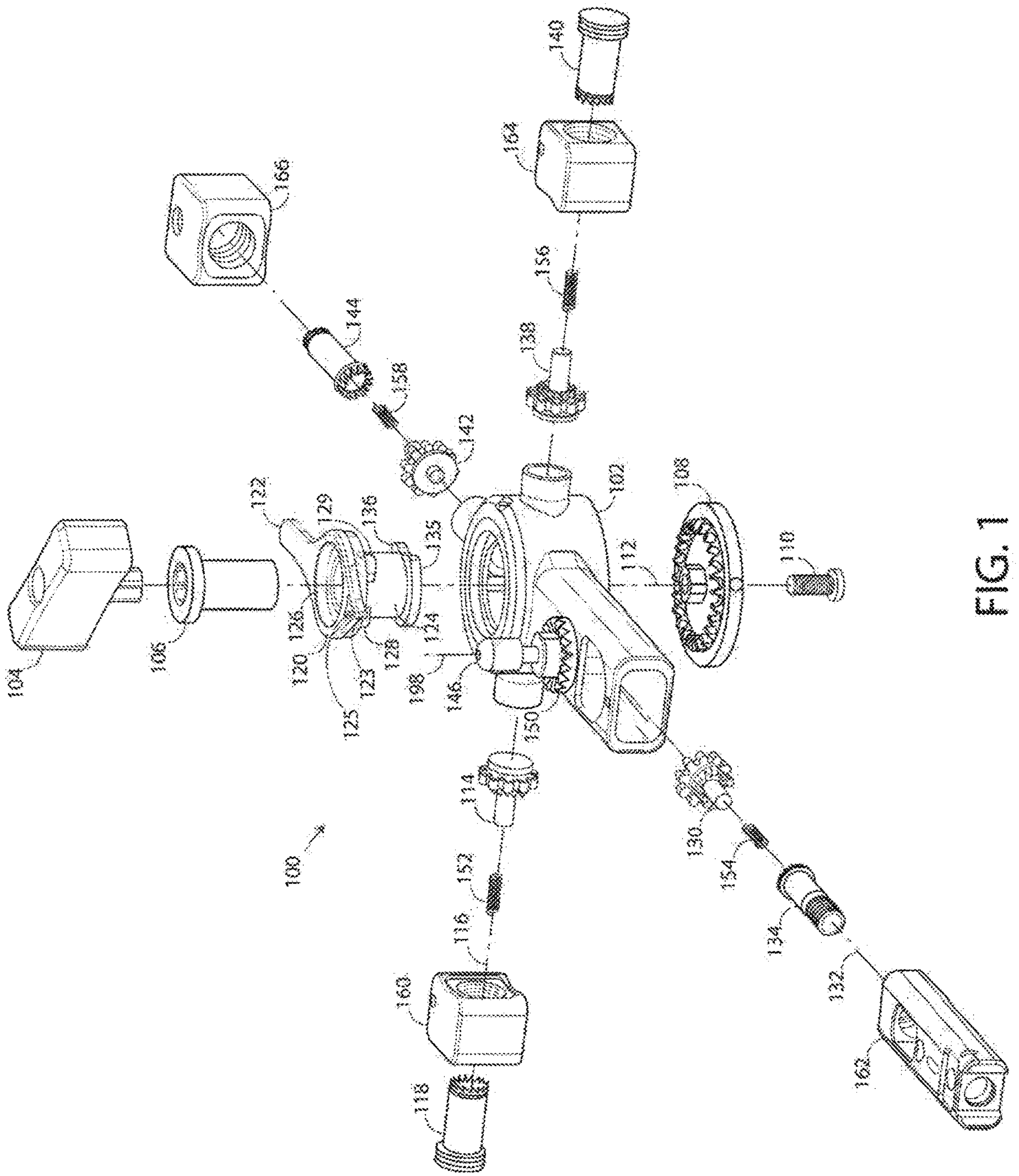
FIG. 1 illustrates an exploded view of an assembly, according to an embodiment of the present disclosure.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. It is also expressly noted that, although shown and described herein largely within the context of lateral surgery in the lumbar spine, the access system of the present invention may be employed in any number of other spine surgery access approaches, including but not limited to posterior, postero-lateral, anterior, and antero-lateral access, and may be employed in the lumbar, thoracic and/or cervical spine, all without departing from the present invention. The surgical access system disclosed herein boasts a variety of inventive features and components that warrant patent protection, both individually and in combination.

Examples described herein include subsystems that enable a surgical retractor, including an assembly, to be used in a surgical procedure. In one example, the assembly includes a dial that is attachable and detachable to a shaft. In this example, the shaft is coupled to a drive gear. The drive gear is configured to rotate along a first axis of the assembly based on movement of the dial. In this example, the assembly also includes a first linking member that is located along a second axis of the assembly. The first linking member includes a gear and is configured to rotate about the second axis based on contact of the gear with the drive gear as the drive gear is rotated via movement of the dial. By way of example, the gear and the drive gear may be bevel gears. The assembly also includes a second linking member located along the second axis. The second linking member is configured to rotate about the second axis based on rotation of the drive gear and a coupling between the first linking member and the second linking member. In one example, the coupling between the first linking member and the second linking member is based on a mating of a first locking element of the first linking member and a second locking element of the second linking member. In one example, the assembly includes a linking member selector that is configured to rotate about the first axis of the assembly. The linking member selector includes a handle for rotating the linking member selector to a position corresponding to the first linking member. The linking member selector includes a cylindrical body that is integrally formed with the handle. The cylindrical body includes an aperture along a longitudinal axis of the cylindrical body. The cylindrical body also includes a protrusion. The protrusion is configured to exert a force on the first linking member based on selection of the position corresponding to the first linking member. The force on the first linking member causes the coupling between the first linking member and the second linking based on a linear movement of the first linking member along the second axis. The aperture is configured to receive the shaft.

Referring now to the figures, FIG. 1 illustrates an exploded view of an example assembly 100. The assembly 100 comprises a body 102. The body 102 is configured to receive a linking member selector 120 along a first axis 112. The linking member selector 120 is configured to receive a shaft 106 that is coupled to a drive gear 108 via a fastener 110. The shaft 106 is configured to receive a dial 104. The body 102 is configured to receive a first linking member 114 along a second axis 116. The body 102 includes a nut 160 that is configured to receive the first linking member 114 and a second linking member 118 along the second axis 116. The second linking member 118 is configured to receive the first linking member 114. The body 102 is configured to receive a third linking member 130 along a third axis 132. The body 102 is configured to receive a center arm 162. The center arm 162 is configured to receive the third linking member 130 and a fourth linking member 134 along the third axis 132. The fourth linking member 134 is configured to receive the third linking member 130. The body 102 is configured to receive a fifth linking member 138 along the second axis 116. The body 102 includes a nut 164 that is configured to receive the fifth linking member 138 and a sixth linking member 140 along the second axis 116. The sixth linking member 140 is configured to receive the fifth linking member 138. The body 102 is configured to receive a seventh linking member 142 along the third axis 132. The body 102 includes a nut 166 that is configured to receive the seventh linking member 142 and an eighth linking member 144 along the third axis 132. The eighth linking member 144 is configured to receive the seventh linking member 142. The body includes a post 146 along a fourth axis 198. As shown in FIG. 1, the first axis 112 is perpendicular to the second axis 116, and the second axis 116 is perpendicular to the third axis 132. Although these axes are shown to be perpendicular to one another in this example assembly 100, other angles between each of the three axes are envisioned.

The linking member selector 120 comprises a handle 122 for rotating the linking member selector 120 about the first axis 112. The linking member selector 120 comprises a cylindrical body 124 that is integrally formed with the handle 122. The cylindrical body 124 includes an aperture 126 along a longitudinal axis of the cylindrical body 124. The cylindrical body 124 comprises a plurality of protrusions 128, 129, 135, and 136 as shown in FIG. 1, and protrusions 137 and 139 not shown in FIG. 1. The linking member selector 120 comprises a pointer 123 and a window 125 for aligning the linking member selector 120 with a position for selecting at least one linking member and for viewing a marking (not shown) on the body 102 that corresponds with the position. In one example, the pointer 123 is configured to align with a position that selects at least one linking member. In this example, one or more markings (not shown) corresponding to one or more positions for selecting at least one linking member are located along a perimeter of the body 102. Continuing with this example, the one or more markings along the perimeter of the body 102 are visible through the window 125 as the linking member selector 120 is rotated about the first axis 112 to a given position associated with a given marking. In one example, the handle 122 is used to rotate the linking member selector 120 to a position that selects at least one linking member of the linking members 114, 130, 138, and 142.

Based on a position selected, at least one of the protrusions of the plurality of protrusions 128, 129, 135, 136, 137, and 139 will exert a force on at least one linking member of the linking members 114, 130, 138, and 142.

For example, based on a desired selection of the first linking member 114, the linking member selector 120 is rotated about the first axis 112 to a given position corresponding to the first linking member 114. As a result of the selection of the first linking member 114, the protrusion 135 will exert a force on the first linking member 114. The force exerted on the first linking member 114 causes the first linking member 114 to move linearly along the second axis 116 from a first position to a second position. In this example, the linear movement of the first linking member 114 from the first position to the second position will result in a coupling between the first linking member 114 and the second linking member 118. In another example, based on rotation of the linking member selector 120 and a selection of the third linking member 130, the protrusion 137 (not shown) will exert a force on the third linking member 130 that causes the third linking member 130 to move linearly along the third axis 132. In this example, the linear movement of the third linking member 130 from a first position to a second position along the third axis 132 will result in a coupling between the third linking member 130 and the fourth linking member 134. In another example, based on rotation of the linking member selector 120 and a selection of the fifth linking member 138, one of the plurality of protrusions 128, 129, 135, 136 and 139 (not shown) will exert a force on the fifth linking member 138 that causes the fifth linking member 138 to move linearly along the second axis 116. In this example, the linear movement of the fifth linking member 138 from a third position to a fourth position along the second axis 116 will result in a coupling between the fifth linking member 138 and the sixth linking member 140. In another example, based on rotation of the linking member selector 120 and a selection of the seventh linking member 142, the protrusion 137 will exert a force on the seventh linking member 142 that causes the seventh linking member 142 to move linearly along the third axis 132. In this example, the linear movement of the seventh linking member 142 from a third position to a fourth position along the third axis 132 will result in a coupling between the seventh linking member 142 and the eighth linking member 144.

As shown in FIG. 1, the aperture 126 of the linking member selector 120 is configured to receive the shaft 106. In one example, the diameter of the aperture 126 and the diameter of the shaft 106 are dimensioned accordingly to allow the shaft 106 to rotate within the aperture 126 and about the first axis 112. In one example, rotation of the shaft 106 is accomplished by movement of the dial 104 when the dial 104 is coupled to the shaft 106. Rotation of the shaft 106 further causes rotation of the drive gear 108 and the linking members 114, 130, 138, and 142.

A spring 152 is interposed between the first linking member 114 and the second linking member 118. A spring 154 is interposed between third linking member 130 and the fourth linking member 134. A spring 156 is interposed between the fifth linking member 138 and the sixth linking member 140. A spring 158 is interposed between the seventh linking member 142 and the eighth linking member 144. In one example, each of the springs 152, 154, 156, and 158 are configured to operate as compression springs. In this example, the springs 152, 154, 156, and 158 are configured to provide a predetermined resistance between the adjacent linking members in order to maintain a distance between the two adjacent linking members that prevents them from coupling with one another. Continuing with this example, the springs 152, 154, 156, and 158 are also configured to compress based on a force exerted by one of the plurality of protrusions 128, 129, 135, 136, 137, and 139 on at least one of the linking members 114, 130, 138, and 142. For example, two adjacent linking members (e.g., first linking member 114 and second linking member 118) are configured to interlock according to predetermined amount of compression on a given spring (e.g., spring 152) according to a force exerted on a given linking member (e.g., linking member 114) as a result of the position of the linking member selector 120.

The nut 160 comprises an internal threaded portion that is configured to engage with a threaded portion of the second linking member 118. In one example, the linking member selector 120 is rotated to a position that corresponds to a selection of the first linking member 114 and thereby causes a coupling between the first linking member 114 and the second linking member 118 as described above. In this example, the dial 104 is rotated in a clockwise direction about the first axis 112 and thereby causes a rotation in a clockwise direction of the drive gear 108 about the first axis 112 and a rotation of the first linking member 114 about the second axis 116. Continuing with this example, as a result of the coupling between the first linking member 114 and the second linking member 118, the second linking member 118 is also rotated about the second axis 116. Based on contact with the internal threaded portion of the nut 160 and the threaded portion of the second linking member 118, the rotational movement of the second linking member 118 is converted to a linear movement of the nut 160 along the second axis 116 and away from the body 102. In this example, as the dial 104 is rotated in a counter-clockwise direction about the first axis 112, the rotational movement of the second linking member 118 is converted to a linear movement of the nut 160 along the second axis 116 and towards the body 102.

The center arm 162 comprises an internal threaded portion that is configured to engage with a threaded portion of the fourth linking member 134. In one example, the linking member selector 120 is rotated to a position that corresponds to selection of the third linking member 130 and thereby causes a coupling between the third linking member 130 and the fourth linking member 134 as described above. In this example, the dial 104 is rotated in a clockwise direction about the first axis 112 and thereby causes a rotation in a clockwise direction of the drive gear 108 about the first axis 112 and a rotation of the third linking member 130 about the third axis 132. Continuing with this example, as a result of the coupling between the third linking member 130 and the fourth linking member 134, the fourth linking member 134 is also rotated about the third axis 132. Based on contact with the internal threaded portion of the center arm 162 and the threaded portion of the fourth linking member 134, the rotational movement of the fourth linking member 134 is converted to a linear movement of the center arm 162 along the third axis 132 and away from the body 102. In this example, as the dial 104 is rotated in a counter-clockwise direction about the first axis 112, the rotational movement of the fourth linking member 134 is converted to a linear movement of the center arm 162 along the third axis 132 and towards the body 102.

The nut 164 comprises an internal threaded portion that is configured to engage with a threaded portion of the sixth linking member 140. In one example, the linking member selector 120 is rotated to a position that corresponds to a selection of the fifth linking member 138 and thereby causes a coupling between the fifth linking member 138 and the sixth linking member 140 as described above. In this example, the dial 104 is rotated in a clockwise direction about the first axis 112 and thereby causes a rotation in a clockwise direction of the drive gear 108 about the first axis 112 and a rotation of the fifth linking member 138 about the second axis 116.

Continuing with this example, as a result of the coupling between the fifth linking member 138 and the sixth linking member 140, the sixth linking member 140 is also rotated about the second axis 116. Based on contact with the internal threaded portion of the nut 164 and the threaded portion of the sixth linking member 140, the rotational movement of the sixth linking member 140 is converted to a linear movement of the nut 164 along the second axis 116 and away from the body 102. In this example, as the dial 104 is rotated in a counter-clockwise direction about the first axis 112, the rotational movement of the second linking member 138 is converted to a linear movement of the nut 164 along the second axis 116 and towards the body 102.

The nut 166 comprises an internal threaded portion that is configured to engage with a threaded portion of the eighth linking member 144. In one example, the linking member selector 120 is rotated to a position that corresponds to a selection of the seventh linking member 142 and thereby causes a coupling between the seventh linking member 142 and the eighth linking member 144 as described above. In this example, the dial 104 is rotated in a clockwise direction about the first axis 112 and thereby causes a rotation in a clockwise direction of the drive gear 108 about the first axis 112 and a rotation of the seventh linking member 142 about the third axis 132. Continuing with this example, as a result of the coupling between the seventh linking member 142 and the eighth linking member 144, the eighth linking member 144 is also rotated about the third axis 132. Based on contact with the internal threaded portion of the nut 166 and the threaded portion of the eighth linking member 144, the rotational movement of the eighth linking member 144 is converted to a linear movement of the nut 166 along the third axis 132 and towards the body 102. In this example, as the dial 104 is rotated in a counter-clockwise direction about the first axis 112, the rotational movement of the eighth linking member 144 is converted to a linear movement of the nut 166 along the third axis 132 and away from the body 102.

In one example, the linking member selector 120 is rotated to a position on the body 102 that corresponds to a selection of the first linking member 114 and a selection of the fifth linking member 138. In this example, a first force is exerted on the first linking member 114 by one of the protrusions 128, 129, 135, 136, and 139 and a second force is exerted on the fifth linking member 138 by another one of the protrusions 128, 129, 135, 136, and 139. As described above, the first force causes a coupling between first linking member 114 and the second linking member 118. Also as described above, the second force causes a coupling between the fifth linking member 138 and the sixth linking member 140. Continuing with this example, the dial 104 is rotated in a clockwise direction about the first axis 112 and thereby causes rotation in a clockwise direction of the drive gear 108 about the first axis 112 and a simultaneous rotation of the first linking member 114 and the fifth linking member 138 about the second axis 116. In this example, as a result of the coupling between the first linking member 114 and the second linking member 118 and the coupling between the fifth linking member 138 and the sixth linking member 140, the second linking member 118 and the sixth linking member 140 are also rotated about the second axis 116. Based on contact with the internal threaded portion of the nut 160 and the threaded portion of the second linking member 118 and contact with the internal threaded portion of the nut 164 and the threaded portion of the sixth linking member 140, the rotational movements of the second linking member 118 and the sixth linking member 140 are converted to linear movements of the nut 160 and the nut 164 along the second axis 116 and away from the body 102. In this example, as the dial 104 is rotated in a counter-clockwise direction about the first axis 112, the rotational movements of the second linking member 118 the sixth linking member 140 are converted to linear movements of the nut 160 and the nut 164 along the second axis 116 and towards the body 102.

As shown in FIG. 1, a post 146 is coupled to the body 102. An anti-rotation feature 150 is secured to the body 102 at a first end of the post 146. In one example, the post 146 is configured to attach the assembly 100 to an external arm (not shown) for securing the assembly 100 in a fixed position during a surgical procedure. In one example, the external arm is an articulating arm comprising one or more sections connected by joints that allow each section to bend or turn independently in different directions.

Figure 2:
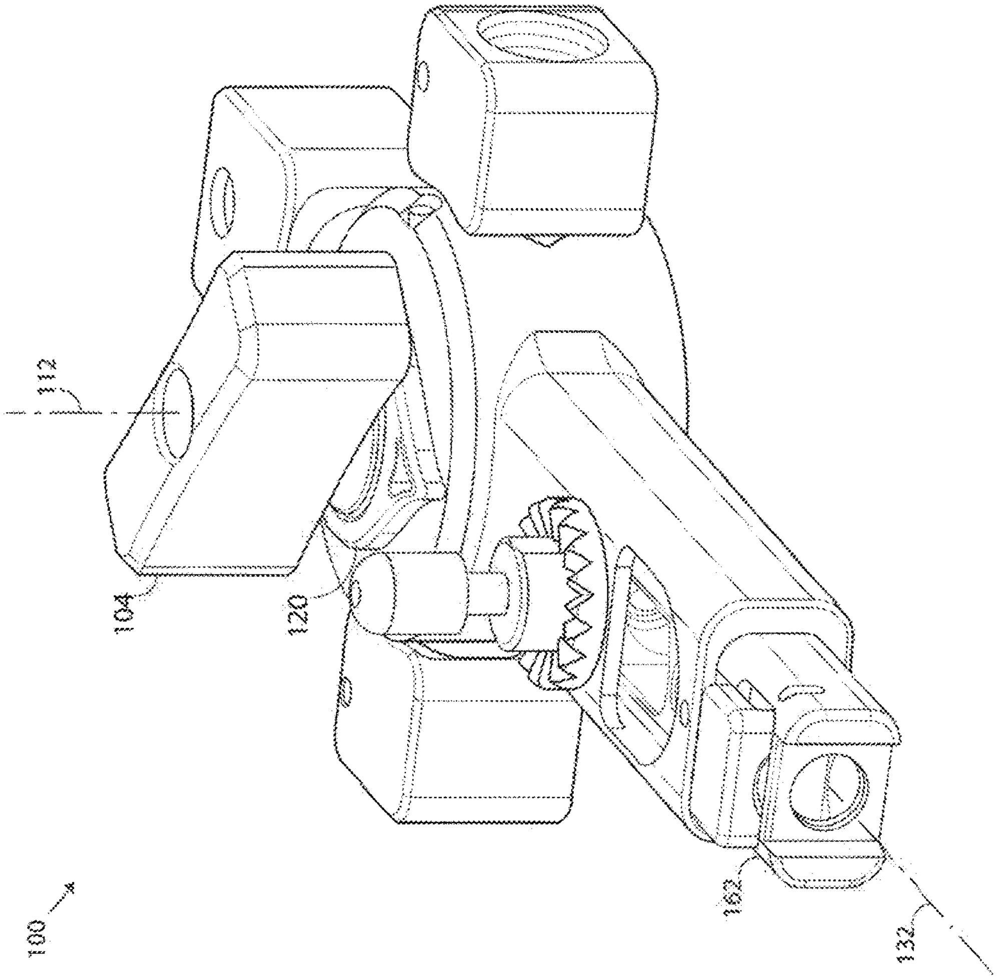
FIG. 2 illustrates another view of the assembly of FIG. 1, according to an embodiment of the present disclosure.

FIG. 2 illustrates an assembled view of the assembly 100 of FIG. 1. As shown in FIG. 2, the linking member selector 120 is in a position corresponding to the seventh linking member 142 (not shown). In this position, based on rotation of the dial 104 about the first axis 112, the rotational movement of the drive gear 108 (not shown) about the first axis 112, the rotational movement of the seventh linking member 142 about the third axis 132, and the rotational movement of the eighth linking member 144 (not shown) about the third axis 132 will be converted to a linear movement of the nut 166 along the third axis 132 as described above.

Figure 3:
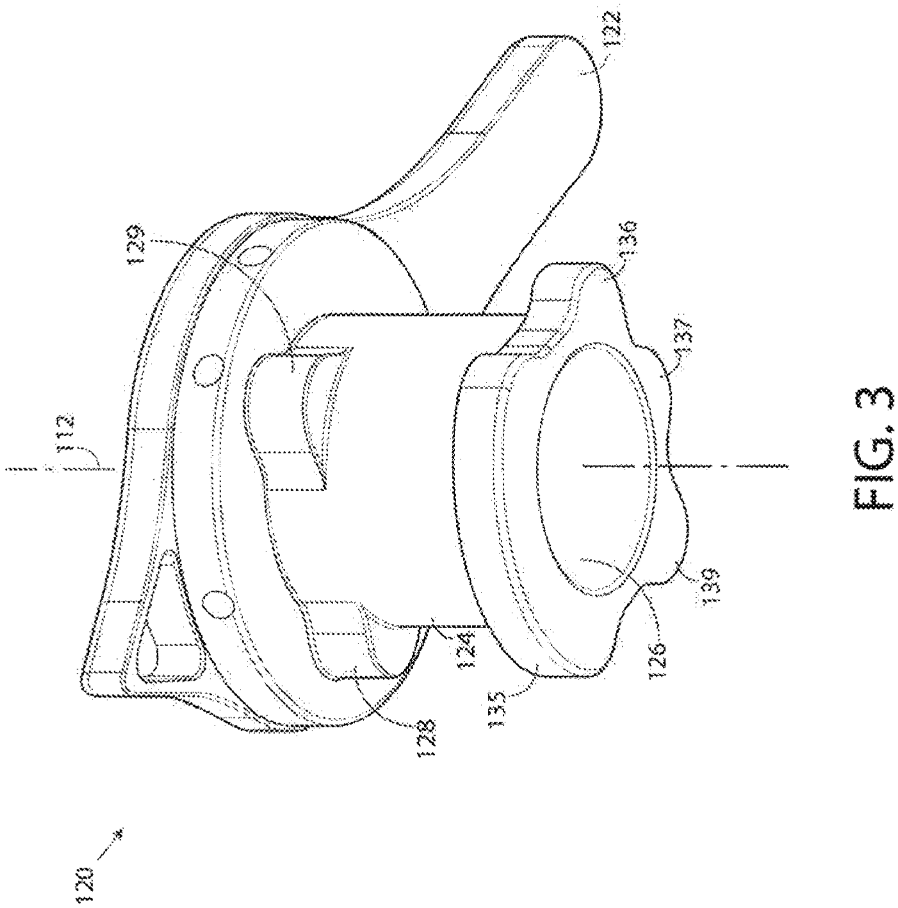
FIG. 3 illustrates a portion of the assembly of FIG. 1, according to an embodiment of the present disclosure.

FIG. 3 illustrates a view of the linking member selector 120 of FIG. 1. As shown in FIG. 3, the linking member selector 120 comprises a plurality of protrusions 128, 129, 135, 136, 137, and 139 located along the cylindrical body 124. In one example, the protrusion 137 is configured to extend along the entire length of the cylindrical body 124. In this example, a contact position of the third linking member 130 along the first axis 116 and a contact position of the seventh linking member 142 along the first axis 116 are at a position along the first axis 112 that is above the contact positions corresponding to each of the protrusions 135, 136, and 139.

The difference between the contact position of the third linking member 130 along the first axis 112 and the contact positions corresponding to each of the protrusions 135, 136, and 139 along the first axis 112 enables only the protrusion 137 to exert a force on the contact position of the third linking member 130. The force exerted on the third liking member 130 results in a coupling between the third linking member 130 and the fourth linking member 134 as described above. Similarly, the difference between the contact position of the seventh linking member 142 along the first axis 112 and the contact position corresponding to each of the protrusions 135, 136, and 139 along the first axis 112 enables only the protrusion 137 to exert a force on the contact position of the seventh linking member 142. The force exerted on the seventh linking member 142 results in a coupling between the seventh linking member 142 and the eighth linking member 144 as described above.

In another example, a contact position of the first linking member 114 along the first axis 112 and a contact position of the fifth linking member 138 along the first axis 112 are at the same position along the first axis 112 as the contact positions corresponding to the protrusions 135, 136, and 139. In this example, the corresponding positions enable only the protrusions 135, 136, and 139 to exert a force on the contact position of the first linking member 114. The force exerted on the first linking member 114 results in a coupling between the first linking member 114 and the second linking member 118 as described above. Similarly, the same position along the first axis 112 of the contact position of the fifth linking member 138 and the contact positions corresponding to the protrusions 135, 136, and 139 enable only the protrusions 135, 136, and 139 to exert a force on the contact position of the fifth linking member 138. The force exerted on the fifth linking member 138 results in a coupling between the fifth linking member 138 and the sixth linking member 140 as described above.

Figure 4:
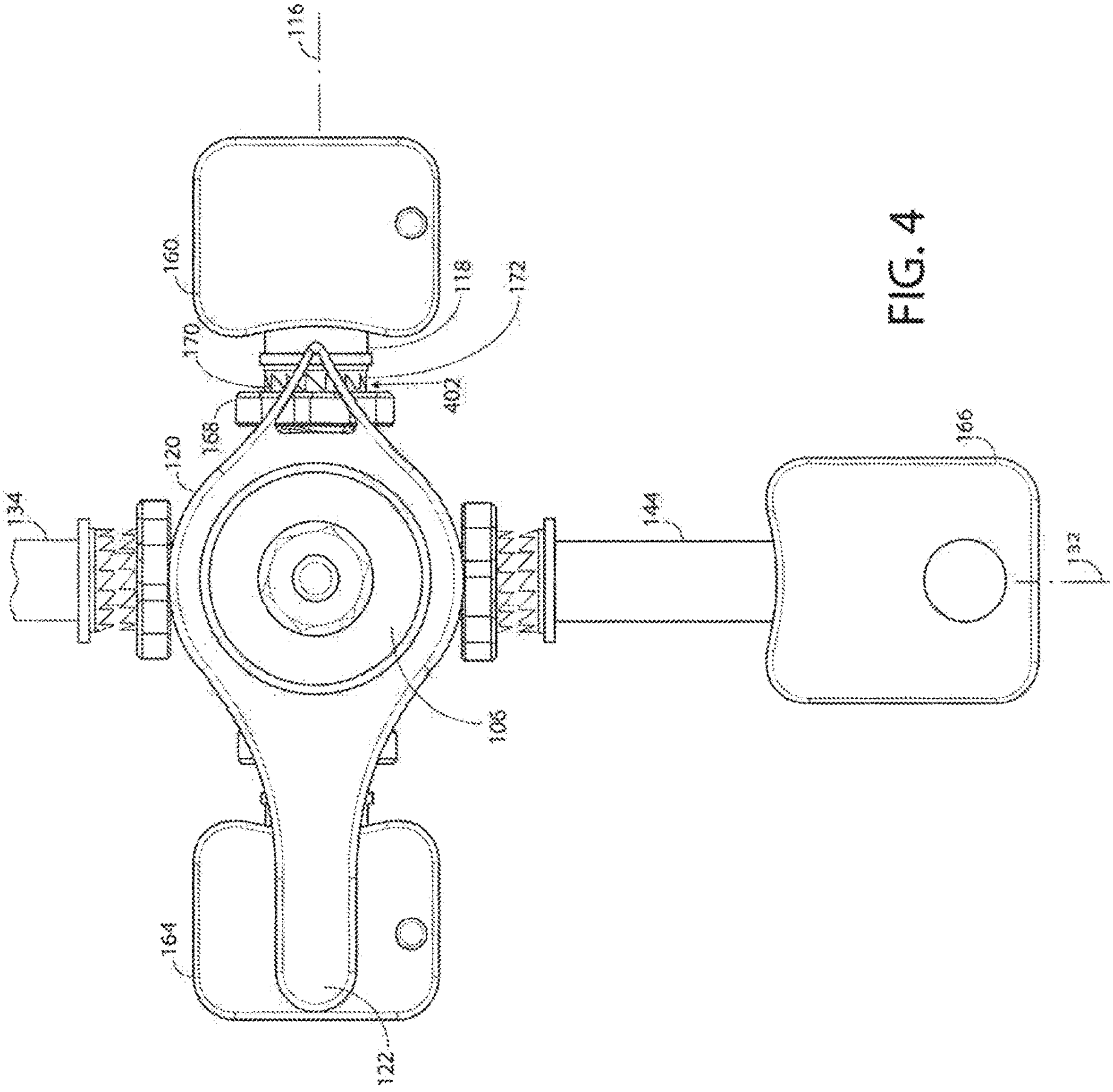
FIG. 4 illustrates a top view of a portion of the assembly of FIG. 1, according to an embodiment of the present disclosure.

FIG. 4 illustrates a top view of a subset of the components of the assembly 100 in FIG. 1. As shown in FIG. 4, the linking member selector 120 has been rotated to a position corresponding to the first linking member 114 (not shown). The first linking member 114 comprises a first gear 168 located along the second axis 116 and configured to rotate based on contact with the drive gear 108 (not shown) of FIG. 1 as the drive gear 108 is rotated. The first linking member 114 includes locking teeth 170 extending from the first gear 168. The second linking member 118 comprises locking teeth 172 extending from the second linking member 118. The locking teeth 172 extending from the second linking member 118 are configured to interlock with the locking teeth 170 extending from the first gear 168 based on a linear movement of the first linking member 118 from a first position along the second axis 116 to a second position along the second axis 116, as shown in FIG. 4. In this scenario, the locking teeth 172 extending from the second linking member 118 are configured to separate from the locking teeth 170 extending from the first gear 168 based on a linear movement of the first linking member 118 from the second position along the second axis 116 to a first position along the second axis 116. In one example, the second linking member 118 comprises a leadscrew configured to translate a rotational movement into a linear movement based on rotation of the drive gear 108 and the coupling between the first linking member 114 and the second linking member 118.

Figure 5:
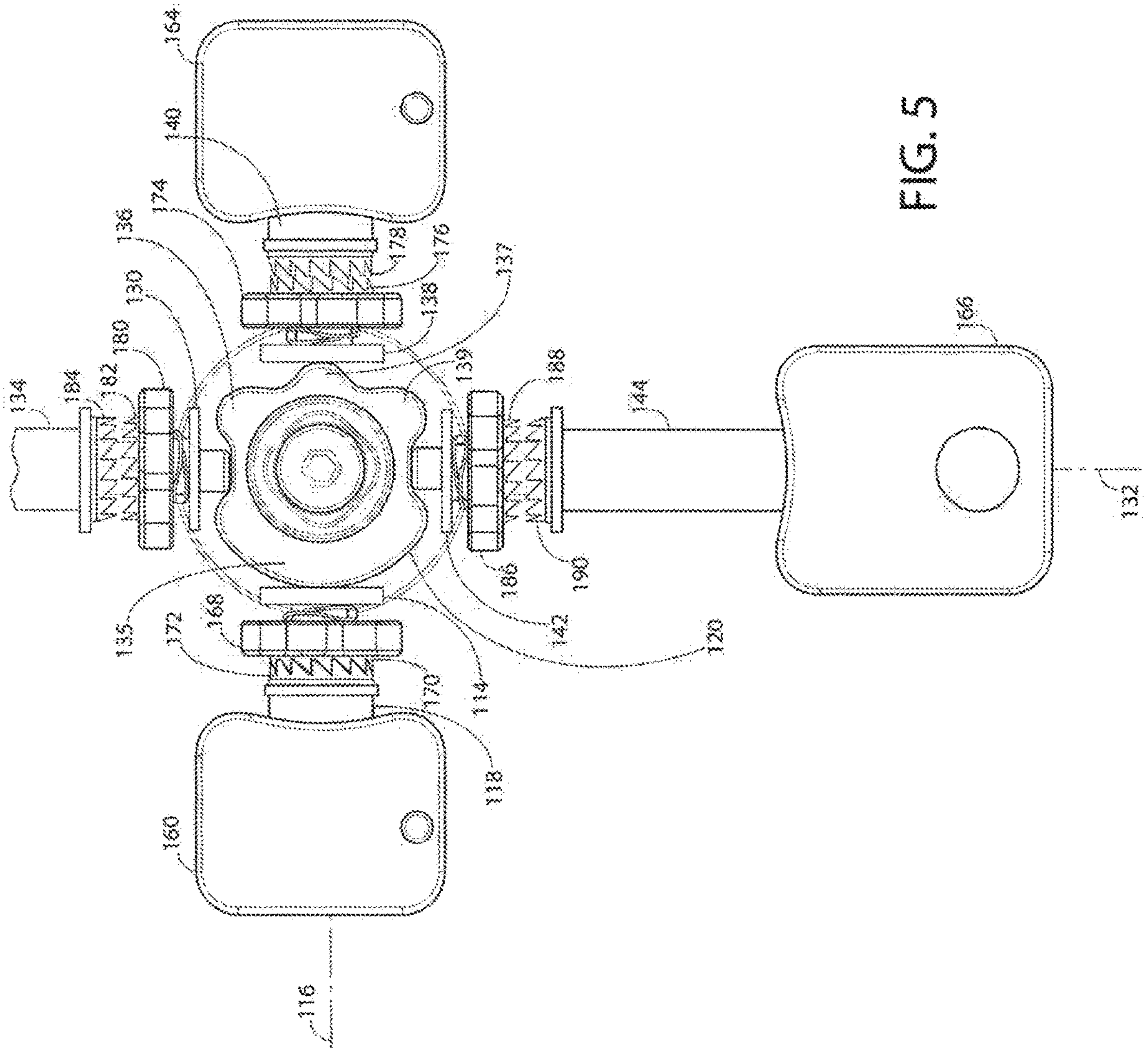
FIG. 5 illustrates a bottom view of a portion of the assembly of FIG. 1, according to an embodiment of the present disclosure.

FIG. 5 illustrates a bottom view that corresponds to the top view of FIG. 4. As shown in FIG. 5, the third linking member 130 comprises a second gear 180 located along the third axis 132 and configured to rotate based on contact with the drive gear 108 (not shown) of FIG. 1 as the drive gear 108 is rotated. The third linking member 130 includes locking teeth 182 extending from the second gear 180. The fourth linking member 134 comprises locking teeth 184. The locking teeth 184 extending from the fourth linking member 134 are configured to interlock with the locking teeth 182 extending from the second gear 180 based on a linear movement of the third linking member 130 from a first position along the third axis 132 to a second position along the third axis 132. The locking teeth 184 extending from the fourth linking member 134 are configured to disengage from the locking teeth 182 extending from the second gear 180 based on a linear movement of the third linking member 130 from the second position along the third axis 132 to the first position along the third axis 132. In one example, the fourth linking member 134 comprises a leadscrew configured to translate a rotational movement into a linear movement based on rotation of the drive gear 108 and the coupling between the third linking member 130 and the fourth linking member 134.

As shown in FIG. 5, the fifth linking member 138 comprises a third gear 174 located along the second axis 116 and configured to rotate based on contact with the drive gear 108 of FIG. 1 as the drive gear 108 is rotated. The fifth linking member 138 includes locking teeth 176 extending from the third gear 174. The sixth linking member 140 also includes locking teeth 178. The locking teeth 178 extending from the sixth linking member 140 are configured to interlock with the locking teeth 176 extending from the third gear based on a linear movement of the fifth linking member 138 from a third position along the second axis 116 to a fourth position, as shown in FIG. 5, along the second axis 116. The locking teeth 176, 178 are configured to disengage based on a linear movement of the fifth linking member 138 from the fourth position along the second axis 116 to the third position along the second axis 116.

As shown in FIG. 5, the seventh linking member 142 comprises a fourth gear 186 located along the third axis 132 and configured to rotate based on contact with the drive gear 108 of FIG. 1 as the drive gear 108 is rotated. The seventh linking member 142 includes locking teeth 188 extending from the fourth gear 186. The eighth linking member 144 also comprises locking teeth 190. The locking teeth 188, 190 are configured to interlock based on a linear movement of the seventh linking member 142 from a third position along the third axis 132 to a fourth position along the third axis 132. The locking teeth 188, 190 are configured to disengage based on a linear movement of the seventh linking member 142 from the fourth position along the third axis 132 to the third position along the third axis 132.

Figure 6:
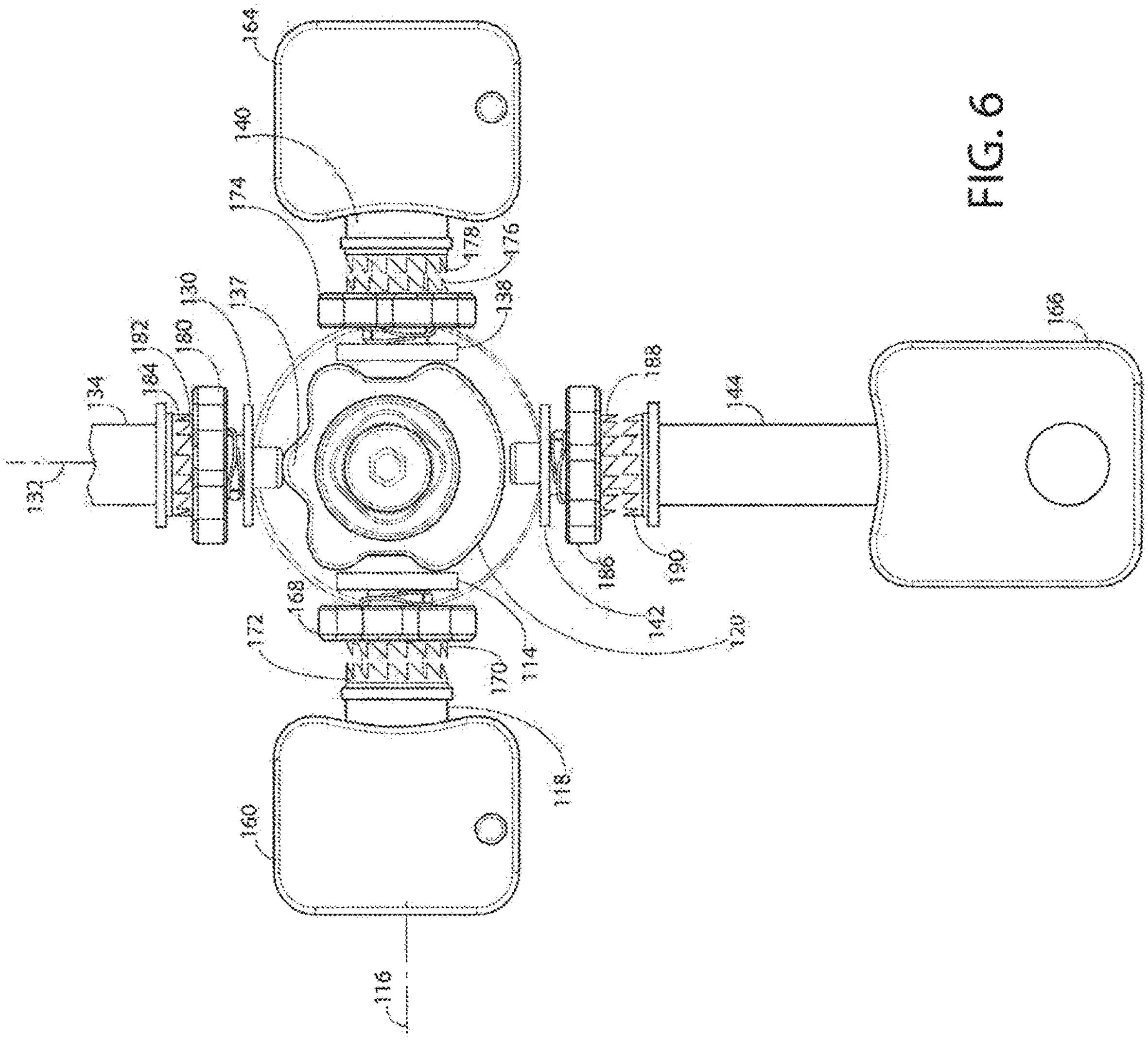
FIG. 6 illustrates a bottom view of a portion of the assembly of FIG. 1, according to an embodiment of the present disclosure.

FIG. 6 illustrates a bottom view of a subset of the components of the assembly 100 in FIGS. 1 and 5. As shown in FIG. 6, the linking member selector 120 has been rotated to a position corresponding to the third linking member 130. In this scenario, the locking teeth 184 extending from the fourth linking member are configured to interlock with the locking teeth 182 extending from the second gear 180 based on a linear movement of the third linking member 130 from a first position along the third axis 132 to a second position, as shown in FIG. 6, along the third axis 132. In this scenario, the locking teeth 182, 184 are configured to disengage based on a linear movement of the third linking member 130 from the second position along the third axis 132 to the first position along the third axis 132.

Figure 7:
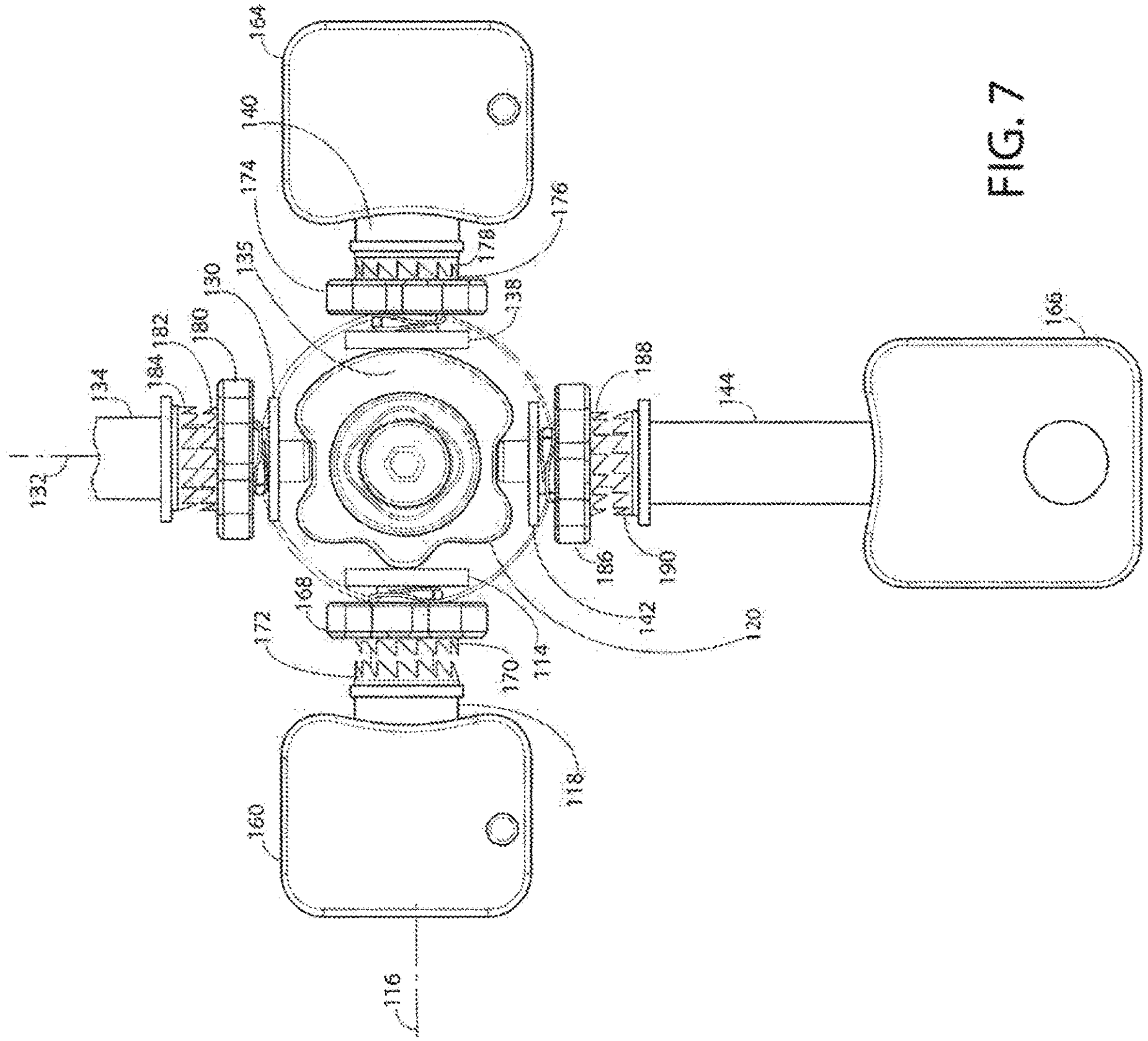
FIG. 7 illustrates a bottom view of a portion of the assembly of FIG. 1, according to an embodiment of the present disclosure.

FIG. 7 illustrates a bottom view of a subset of the components of the assembly 100 in FIGS. 1 and 5. As shown in FIG. 7, the linking member selector 120 has been rotated to a position corresponding to the fifth linking member 138. In this scenario, the locking teeth 176, 178 are configured to interlock based on a linear movement of the fifth linking member 138 from a third position along the second axis 116 to a fourth position, as shown in FIG. 7, along the second axis 116. In this scenario, the locking teeth 176, 178 are configured to disengage based on a linear movement of the fifth linking member 138 from the fourth position along the second axis 116 to a third position along the second axis 116.

Figure 8:
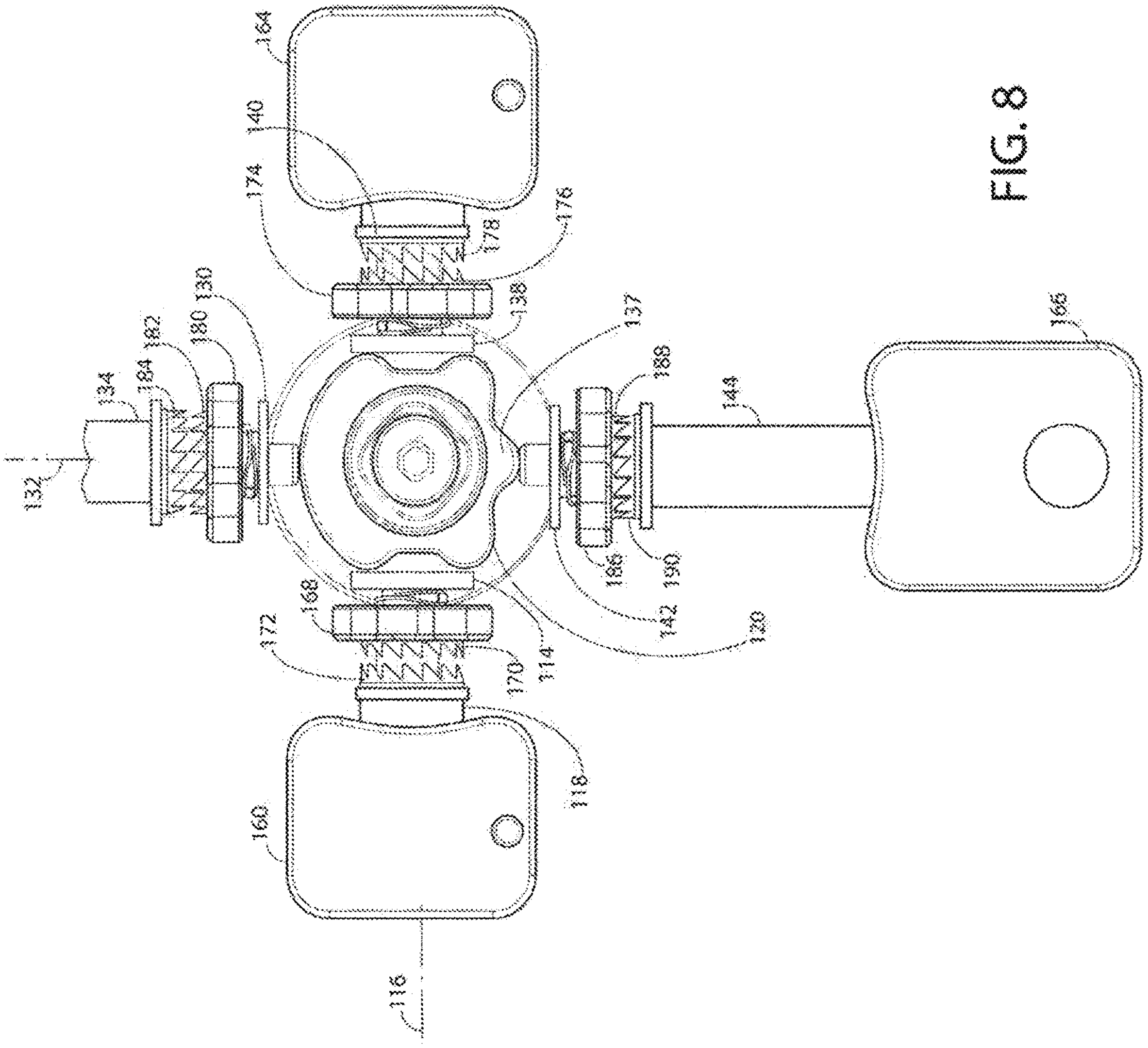
FIG. 8 illustrates a bottom view of a portion of the assembly of FIG. 1, according to an embodiment of the present disclosure.

FIG. 8 illustrates a bottom view of a subset of the components of the assembly 100 in FIGS. 1 and 5. As shown in FIG. 8, the linking member selector 120 has been rotated to a position corresponding to the seventh linking member 142. In this scenario, the locking teeth 190 extending from 144 are configured to interlock with the locking teeth 188 extending from the seventh linking member 142 based on a linear movement of the seventh linking member 142 from a third position along the third axis 132 to a fourth position, as shown in FIG. 8, along the third axis 132. In this scenario, the locking teeth 188, 190 are configured to disengage based on a linear movement of the seventh linking member 142 from the fourth position along the third axis 132 to the third position along the third axis 132.

Figure 9:
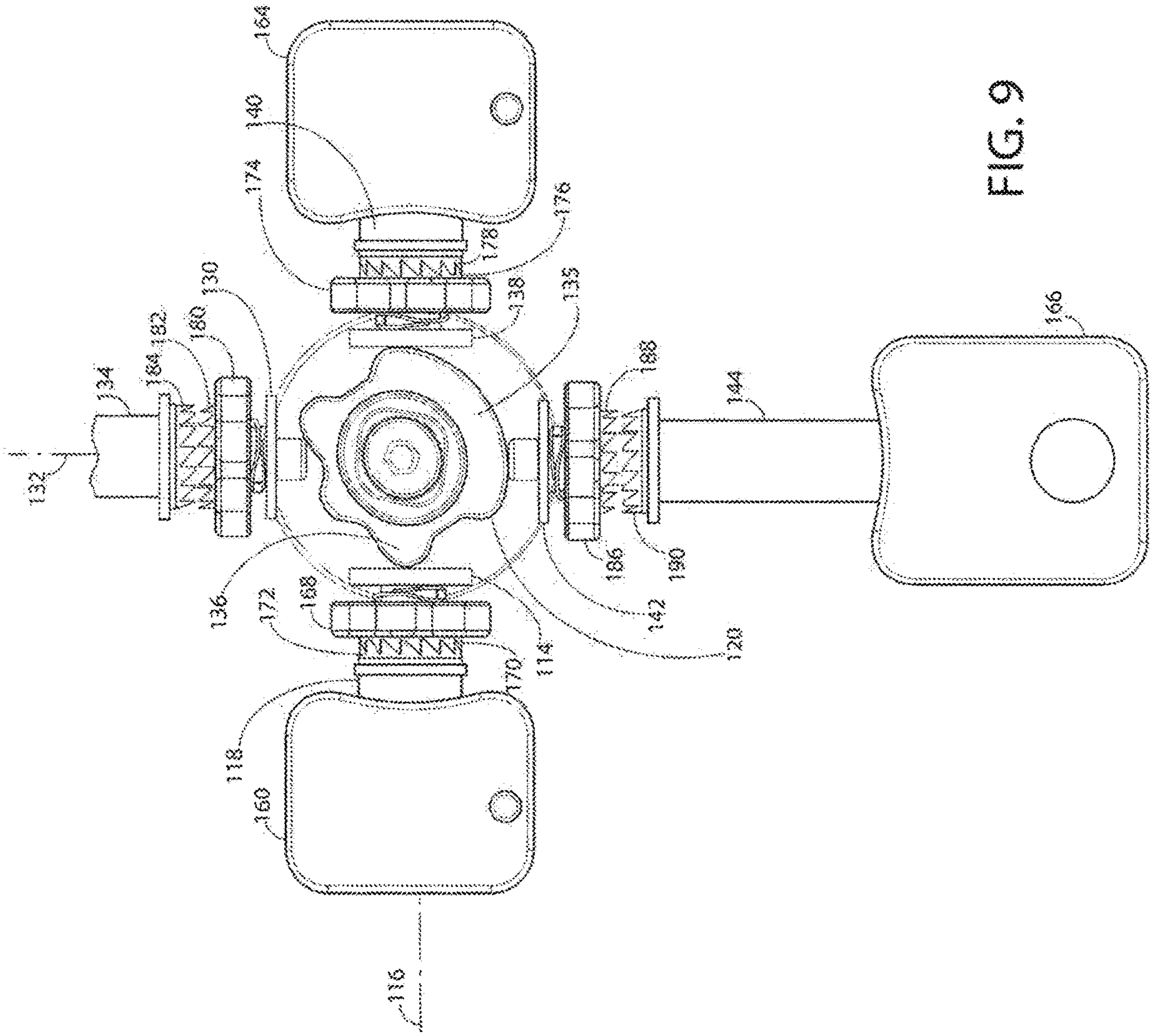
FIG. 9 illustrates a bottom view of a portion of the assembly of FIG. 1, according to an embodiment of the present disclosure.

FIG. 9 illustrates a bottom view of a subset of the components of the assembly 100 in FIGS. 1 and 5. As shown in FIG. 9, the linking member selector 120 has been rotated to a position corresponding to the first linking member 114 and the fifth linking member 138. In this scenario, the locking teeth 172 extending from the second linking member 118 are configured to interlock with or disengage from the locking teeth 170 extending from the first gear 168 as described above. Further, in this scenario, the locking teeth 178 extending from the sixth linking member 140 are configured to interlock with or disengage from with the locking teeth 176 extending from the third gear 174 as described above.

Figure 10:
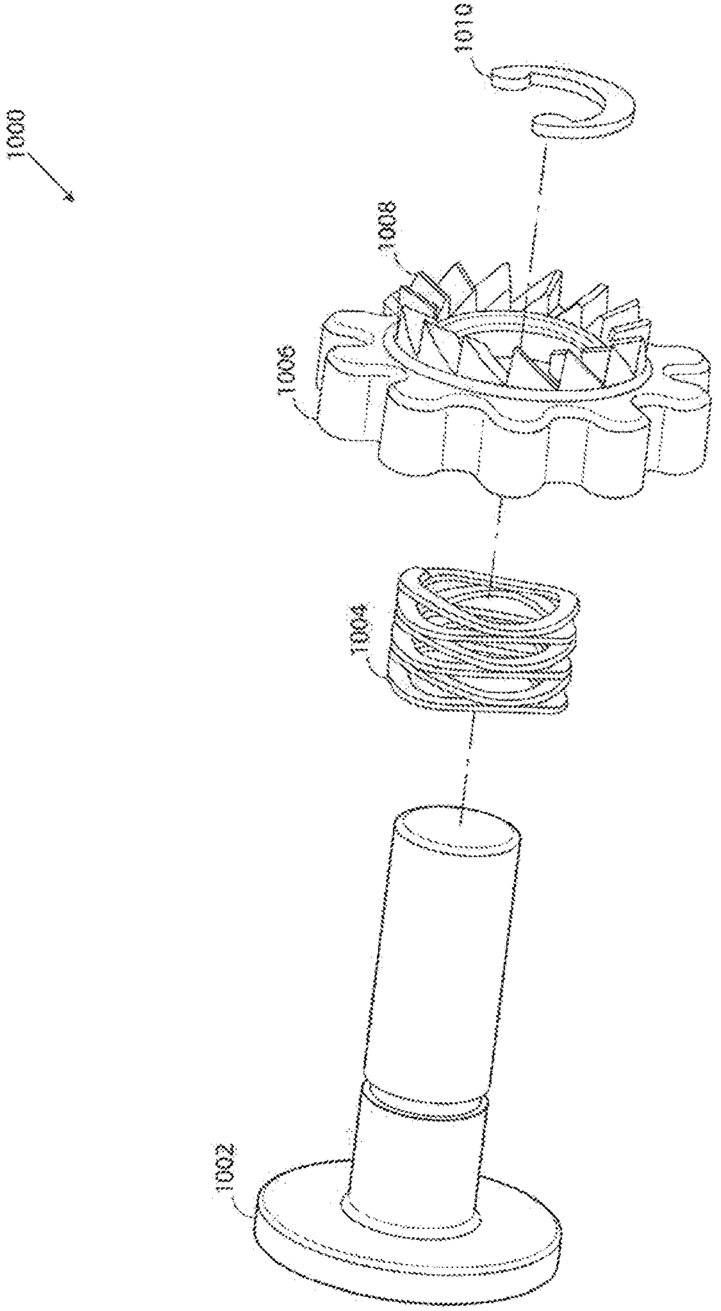
FIG. 10 illustrates an example pinion assembly according to an embodiment of the present disclosure.

FIG. 10 illustrates an example pinion sub-assembly 1000. The pinion sub-assembly 1000 comprises a linking member 1002, a spring 1004, a gear 1006, and a retaining element 1010. The gear 1006 comprises locking teeth 1008. The linking member 1002 is configured to receive the spring 1004, the gear 1006, and the retaining element 1010. The retaining element 1010 is configured to retain the spring 1004 and the gear 1006 from advancing past a given position along the linking member 1002.

In one example, the linking members 114, 130, 138, and 142, as described above, comprise all of the components of the pinion sub-assembly 1000. In this example, the linking member 1002 operates in a similar manner as described with respect to the linking members 114, 130, 138, and 142. Continuing with this example, the gear 1006 and the locking teeth 1008 also operate in a similar manner as described with the first gear 168 and the locking teeth 170, the second gear 180 and the locking teeth 182, the third gear 174 and the locking teeth 176, and the fourth gear 186 and the locking teeth 188, respectively. Further, in this example, the spring 1004 is configured to compress based on a force exerted by a protrusion (e.g., one of the protrusions 128, 129, 135, 136, 137, and 139 of FIG. 3) on the linking member 1002 (e.g., one of the linking members 114, 130, 138, 142 of FIG. 1) and based on a rotational position of the locking teeth 1008 with respect to the locking teeth of another linking member.

In one scenario, referring to FIG. 5, if the tips of the locking teeth 170 and the tips locking teeth 172 are in a given rotational position along the second axis 116 as the first linking member 114 is moved linearly along the first axis 116 towards the second linking member 118, then it is possible that the locking teeth 170 and 172 will be unable to interlock with one another as shown in FIG. 5. Further, it is also possible that the linking member selector 120 could also become temporarily stuck in this position based on the tips of the locking teeth 170 and 172 preventing the locking teeth 170 and 172 from interlocking. In order to overcome this scenario, referring back to FIG. 10, the spring 1004 is compressed as the linking member 1002 is moved along a linear axis towards another linking member while the tips of the locking teeth 1008 encounter the tips of the locking teeth of another linking member at a rotational position that prevents the locking teeth 1008 from interlocking with the locking teeth of another linking member. In this scenario, upon a rotation of the dial 104 and the drive gear 108, the locking teeth 1008 (e.g., the locking teeth 170 of FIG. 5) would rotate about an axis just enough where the tips of the locking teeth 1008 are no longer in direct contact with the tips of the locking teeth corresponding to another linking member. Continuing with this scenario, based on a rotational movement of the linking member 1002, the stored mechanical energy in the spring 1004 would be released and thereby cause the linking member 1002 (e.g., the linking member 114 of FIG. 5) to further move along the linear axis to a given position that enables the locking teeth 1008 (e.g., the locking teeth 170 of FIG. 5) to interlock with the locking teeth (e.g., the locking teeth 172 of FIG. 5) of another linking member (e.g., the linking member 118 of FIG. 5).

Figure 11:
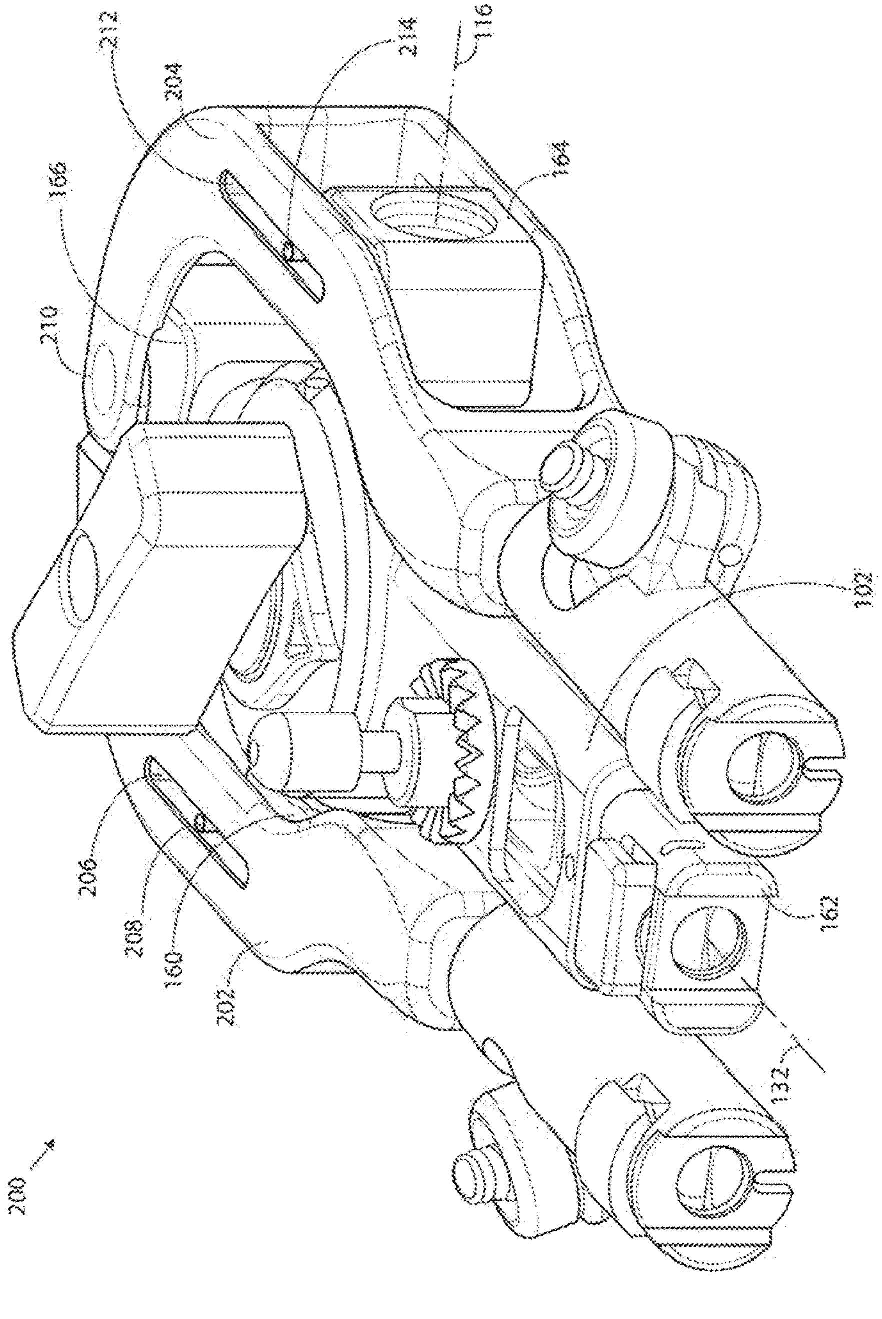
FIG. 11 illustrates a surgical retractor, according to an embodiment of the present disclosure.

FIG. 11 illustrates an example surgical retractor 200. The surgical retractor 200 comprises the assembly 100 of FIG. 1, a right arm assembly 202, and a left arm assembly 204. As shown in FIG. 11, the right arm assembly 202 comprises a channel 206. The channel 206 is configured to receive a pin 208 that is coupled to the nut 160 of FIG. 1. The right arm assembly 202 comprises an aperture for receiving a pin 210 that is coupled to the nut 166 of FIG. 1. The left arm assembly 204 comprises a channel 212. The channel 212 is configured to receive a pin 214 that is coupled to nut 164 of FIG. 1. The left arm assembly 204 comprises an aperture for also receiving the pin 210 that is coupled to the nut 166 of FIG. 1.

In one example, based on the position of linking member selector 120 corresponding to first linking member 114 (not shown) and rotation of the dial 104 as described above, the nut 160 is configured to move away from or towards the body 102 about the second axis 116. In this example, the right arm assembly 202 is configured to move away from or towards the body 102 based on the force exerted by the pin 208 on the right arm assembly 202 in addition to the right arm assembly 202 being configured to pivot around the pin 210.

In one example, based on the position of linking member selector 120 corresponding to seventh linking member 142 (not shown) and rotation of the dial 104 as described above, the nut 166 is configured to move away from or towards the body 102 about the third axis 132. In this example, the right arm assembly 202 and left arm assembly 204 are configured to move away from or towards the body 102 based on the force exerted by the pin 210 on the right arm assembly 202 and the left arm assembly 204.

In one example, based on the position of linking member selector 120 corresponding to fifth linking member 138 (not shown) and rotation of the dial 104 as described above, the nut 164 is configured to move away from or towards the body 102 along the second axis 116. In this example, the left arm assembly 204 is configured to move away from or towards the body 102 based on the force exerted by the pin 214 on the left arm assembly 204 in addition to the left arm assembly 204 being configured to pivot around the pin 210.

In one example, based on the position of linking member selector 120 corresponding to first linking member 114 and the fifth linking member 138 (not shown) and rotation of the dial 104 as described above, the nut 160 and the nut 164 are configured to move away from or towards the body 102 along the second axis 116. In this example, the right arm assembly 202 and the left arm assembly 204 are configured to move away from or towards the body 102 based on the force exerted by the pin 208 on the right arm assembly 202, the force exerted by the pin 214 on the left arm assembly 204, the right arm assembly 202 being configured to pivot around the pin 210, and the left arm assembly 204 being configured to pivot around the pin 210.

In one example, the right arm assembly 202, the left arm assembly 204, and the center arm 162 are each configured to receive a retractor blade for use during a surgical procedure. By way of example, the retractor blades may be composed of any material suitable for introduction into the human body, including but not limited to stainless steel, aluminum, titanium, and/or clear polycarbonate, that would ensure rigidity during tissue retraction. The retractor blades may be optionally coated with a carbon fiber reinforced coating to increase strength and durability.

The blades may be optionally constructed from partially or wholly radiolucent materials (e.g., aluminum, PEEK, carbon-fiber, and titanium) to improve the visibility of the surgeon during imaging (e.g., radiographic, MRI, CT, fluoroscope, etc.). The retractor blades may also be composed of a material that would destruct when autoclaved (such as polymer containing a portion of glass particles), which may be advantageous in preventing the unauthorized re-use of the blades (which would be provided to the user in a sterile state). The retractor blades may be provided in any number of suitable lengths, depending upon the anatomical environment and surgical approach, such as (by way of example only) the range from 20 mm to 150 mm. Based on this range of sizes, the assembly 100 of FIG. 1 is extremely versatile and may be employed in any of a variety of desired surgical approaches, including but not limited to lateral, posterior, postero-lateral, anterior, and antero-lateral, by simply selecting the desired size retractor blades and attaching them to the surgical retractor 200.

In one example, the retractor blades may be equipped with various additional features or components. By way of example only, one or more of the retractor blades may be equipped with a retractor extender, such as a wide retractor extender or a narrow retractor extender. The retractor extenders extend from the retractor blades to form a protective barrier to prevent the ingress or egress of instruments or biological structures (e.g., nerves, vasculature, organs, etc. . . . ) into or out of an operative corridor. Depending upon the anatomical setting and surgical approach, one or more of the retractor blades may be equipped with a shim element. In one example, the shim element has a distal tapered region which may be advanced into tissue (e.g. bone, soft tissue, etc.) for the purpose of anchoring the retractor blades and/or advanced into a disc space to distract the adjacent vertebral bodies (thereby restoring disc height). In similar fashion to the retractor extenders, the shim element also forms a protective barrier to prevent the ingress or egress of instruments or biological structures (e.g., nerves, vasculature, etc.) into or out of the operative corridor.

In one example, the retractor extenders and/or the shim element may be made out any material suitable for use in the human body, including but not limited to biologically compatible plastic and/or metal, preferably partially or wholly radiolucent in nature material (such as aluminum, PEEK, carbon-fibers and titanium). Construction from plastic or thin metal provides the additional benefit of allowing the shim and/or the retractor extenders to be collapsed into a compressed or low profile configuration at the skin level as the element is inserted, and then expanded once it is below skin level and within the operative corridor. In another example, the retractor extenders may have symmetric narrow configurations and/or broad configurations and/or an asymmetric configuration of narrow and broad elements. For example, any or all of the retractor extenders may be provided with a lateral section, a narrow configuration, and/or a lateral section. The retractor extenders and/or the shim element may be composed of a material that would destruct when autoclaved (such as polymer containing a portion of glass particles), which may be advantageous in preventing the unauthorized re-use of the retractor extenders and/or the shim element (which would be provided to the user in a sterile state). Slits may also be provided on the shim to improve flexibility. The retractor extenders and/or the shim element may have a parabolic concave curvature.

In one example, each of the retractor extenders and/or the shim element may be equipped with a mechanism to selectively and releasably engage with the respective retractor blades. By way of example only, this may be accomplished by configuring the retractor extenders and/or the shim element with a tab element capable of engaging with corresponding ratchet-like grooves along the inner-facing surfaces of the retractor blades. Each of the retractor extenders and/or the shim element is provided with a pair of engagement elements having, by way of example only, a generally dove-tailed cross-sectional shape. The engagement elements are dimensioned to engage with receiving portions on the respective retractor blades. In a preferred embodiment, each of the retractor extenders and/or the shim element may be provided with an elongate slot for engagement with an insertion tool. Each tab member is also equipped with an enlarged tooth element which engages within corresponding grooves provided along the inner surface of the retractor blades. On the wide retractor extenders, each includes a center portion flanked by a pair of lateral sections, which effectively increase the width of the retractor blades.

In another example, any or all of the retractor blades, the retractor extenders, and/or the shim element may be provided with one or more electrodes (preferably at or near their distal regions) equipped for use with a nerve surveillance system, such as, by way of example, the type shown and described in Int'l Patent App. Ser. Nos. PCT/US02/30617 filed on Sep. 25, 2002, filed on Jul. 11, 2002, Int'l Patent App. Ser. No. PCT/US2008/004427, filed Apr. 3, 2008 ("Neurophysiology Monitoring Patents") the entire contents of which are each expressly incorporated by reference herein. Such a nerve surveillance system is capable of detecting the existence of (and optionally the distance and/or direction to) neural structures during the retraction of tissue by detecting the presence of nerves by applying a stimulation signal to electrodes and monitoring the evoked EMG signals from the myotomes associated with the nerves in the vicinity of the retractor blades. In so doing, the system as a whole (including the surgical retractor 200) may be used to form an operative corridor through (or near) any of a variety of tissues having such neural structures, particularly those which, if contacted or impinged, may otherwise result in neural impairment for the patient. In this fashion, the access system of the surgical retractor 200 may be used to traverse tissue that would ordinarily be deemed unsafe or undesirable, thereby broadening the number of manners in which a given surgical target site may be accessed.

Any of the features or attributes of the above described embodiments and variations can be used in combination with any of the other features and attributes of the above described embodiments and variations as desired. Various modifications, additions and other alternative embodiments are possible without departing from the true scope and spirit. The embodiments presented herein were chosen and described to provide an illustration of various principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

The invention claimed is:

1. A surgical retractor comprising:

a first arm assembly;

a second arm assembly; and an adjustment assembly, comprising:

a selector configured to be moved between two or more positions associated with the first arm assembly, the second arm assembly or both of the first arm assembly and the second arm assembly; and a drive mechanism, wherein the first arm assembly, the second arm assembly, or both of the first arm assembly and the second arm assembly are configured to adjust relative to the selector in response to actuation of the drive mechanism and based on a position of the selector; and wherein the adjustment assembly comprises:

a dial;

a shaft coupled to the dial;

a drive gear coupled to the shaft, wherein the drive gear is configured to rotate along a first axis based on movement of the dial;

a first linking member located along a second axis and configured to rotate along the second axis based on contact with the drive gear as the drive gear is rotated, wherein the second axis is perpendicular to the first axis;

a second linking member located along the second axis and configured to rotate about the second axis based on rotation of the drive gear and a coupling between the first linking member and the second linking member; and wherein the selector is configured to rotate about the first axis.

2. The surgical retractor of claim 1, comprising:

a third arm assembly, wherein the selector is configured to be moved to a position associated with the third arm assembly, wherein the third arm assembly is configured to adjust relative to the selector in response to actuation of the drive mechanism when the selector is at the position associated with the third arm assembly.

3. The surgical retractor of claim 2, wherein the adjustment assembly comprises:

an adjustable member coupled with the first arm assembly and the second arm assembly, wherein the selector is configured to be moved to a position associated with the adjustable member, wherein the adjustable member, the first arm assembly, and the second arm assembly are configured to adjust relative to the selector in response to actuation of the drive mechanism when the selector is at the position associated with the adjustable member.

4. The surgical retractor of claim 1, wherein the selector comprises a handle for rotating the selector and selecting at least a position corresponding to the first linking member, and a cylindrical body integrally formed with the handle.

5. The surgical retractor of claim 4, wherein the cylindrical body comprises an aperture along a longitudinal axis of the cylindrical body and at least one protrusion configured to exert a force on the first linking member based on selection, via the handle, of the position corresponding to the first linking member, wherein the force on the first linking member causes the coupling between the first linking member and the second linking member, wherein the aperture is configured to receive the shaft.

6. The surgical retractor of claim 1, wherein the coupling between the first linking member and the second linking member is based on a linear movement of the first linking member from a first position along the second axis to a second position along the second axis.

7. The surgical retractor of claim 1, wherein the at least one protrusion includes a first protrusion configured to exert a force on the first linking member based on selection, via the handle, of the position corresponding to the first linking member, wherein the at least one protrusion includes a second protrusion.

8. The surgical retractor of claim 7, wherein the adjustment assembly comprises:

a third linking member located along a third axis and configured to rotate about the third axis based on contact with the drive gear as the drive gear is rotated, wherein the third axis is perpendicular to the first axis and the second axis;

a fourth linking member located along the third axis and configured to rotate about the third axis based on rotation of the drive gear and a coupling between the third linking member and the fourth linking member, wherein the at least a position corresponding to the first linking member comprises a first position corresponding to the first linking member and a second position corresponding to the third linking member, wherein the second protrusion is configured to exert a force on the third linking member based on selection, via the handle, of the second position, wherein the force on the third linking member causes the coupling between the third linking member and the fourth linking member.

9. The surgical retractor of claim 8, wherein the coupling between the third linking member and the fourth linking member is based on a linear movement of the third linking member from a first position along the third axis to a second position along the third axis.

10. The surgical retractor of claim 9, wherein the adjustment assembly comprises:

a fifth linking member located along the second axis and configured to rotate about the second axis based on contact with the drive gear as the drive gear is rotated;

a sixth linking member located along the second axis and configured to rotate about the second axis based on rotation of the drive gear and a coupling between the fifth linking member and sixth linking member, wherein the at least a position corresponding to the first linking member comprises the first position corresponding to the first linking member, the second position corresponding to the third linking member, and a third position corresponding to the fifth linking member, wherein the first protrusion is configured to exert a force on the fifth linking member based on selection, via the handle, of the third position, wherein the force on the fifth linking member causes the coupling between the fifth linking member and the sixth linking member.

11. The surgical retractor of claim 10, wherein the coupling between the fifth linking member and the sixth linking member is based on a linear movement of the fifth linking member from a third position along the second axis to a fourth position along the second axis.

12. The surgical retractor of claim 11, wherein the adjustment assembly comprises:

a seventh linking member located along the third axis and configured to rotate about the third axis based on contact with the drive gear as the drive gear is rotated;

an eighth linking member located along the third axis and configured to rotate about the third axis based on rotation of the drive gear and a coupling between the seventh linking member and the eighth linking member, wherein the at least a position corresponding to the first linking member comprises the first position corresponding to the first linking member, the second position corresponding to the third linking member, the third position corresponding to the fifth linking member, and a fourth position corresponding to the seventh linking member, wherein the second protrusion is configured to exert a force on the seventh linking member based on selection, via the handle, of the fourth position, wherein the force on the seventh linking member causes the coupling between the seventh linking member and the eighth linking member.

13. The surgical retractor of claim 12, wherein the coupling between the seventh linking member and the eighth linking member is based on a linear movement of the seventh linking member from a third position along the third axis to a fourth position along the third axis.

14. The surgical retractor of claim 1, wherein the adjustment assembly comprises a post configured to attach the assembly to an external arm, wherein the post is located along a fourth axis parallel and offset to the first axis.

15. The surgical retractor of claim 14, wherein the adjustment assembly comprises locking teeth secured to the assembly at a first end of the post.

* * * * *